US008747793B2

(12) United States Patent
Yang et al.

(10) Patent No.: US 8,747,793 B2
(45) Date of Patent: Jun. 10, 2014

(54) HOLLOW SPHERE WITH MESOPOROUS STRUCTURE AND METHOD FOR MANUFACTURING THE SAME

(75) Inventors: Chia-Min Yang, Hsinchu (TW); Li-Lin Chang, Hsinchu (TW); Pei-Hsin Ku, Hsinchu (TW); Nien-Chu Lai, Hsinchu (TW); Kuan-Yi Li, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 174 days.

(21) Appl. No.: 13/204,143

(22) Filed: Aug. 5, 2011

(65) Prior Publication Data
US 2012/0251825 A1    Oct. 4, 2012

(30) Foreign Application Priority Data

Mar. 28, 2011    (TW) .............................. 100110568 A

(51) Int. Cl.
*C01B 33/00* (2006.01)
(52) U.S. Cl.
USPC ........................... 423/335; 423/339; 428/402
(58) Field of Classification Search
USPC .................................. 423/335, 339; 428/402
See application file for complete search history.

(56) References Cited

U.S. PATENT DOCUMENTS

| 5,220,101 | A | 6/1993 | Beck et al. | |
|---|---|---|---|---|
| 2010/0015026 | A1* | 1/2010 | Yang et al. | 423/328.1 |
| 2010/0015027 | A1* | 1/2010 | Yang et al. | 423/328.1 |

FOREIGN PATENT DOCUMENTS

CN        10-2126729    *    7/2011

OTHER PUBLICATIONS

Translation of Thesis of Li-Lin Chang, Jul. 2009, pp. 32,33,35,38-43,59-63,74-79 and abstract.*
C. T. Kresge, M. E. Leonowicz, W. J. Roth, J. C. Vartuli, and J. S. Beck; Ordered Mesoporous Molecular Sieves Synthesized by a Liq-uid-Crystal Template Mechanism; *Letter to Nature*; Oct. 22, 1992; p. 710-p. 712; vol. 359; Nature Publishing Group.
J. S. Beck, J. C. Vartuli, W. J. Roth, M. E. Leonowicz, C. T. Kresge, K. D. Schmitt, C. T. W. Chu, D. H. Olson, and E. W. Sheppard; A New Family of Mesoporous Molecular Sieves Prepared with Liquid Crystal Templates; *Journal of the American Chemical Society*; 1992; p. 10834-p. 10843; vol. 114, No. 27; ACS Publications.
Zhang Feng, Yongsheng Li, Dechao Niu, Liang Li, Wenru Zhao, Hangrong Chen, Lei Li, Jianhua Gao, Meiling Ruan, and Jianlin Shi;A Facile Route to Hollow Nanospheres of Mesoporous Silica with Tunable Size; *The Royal Society of Chemistry*; May 1, 2008; p. 2629-p. 2631; Chemical Communications.
Genggeng Qi, Yanbing Wang, Luis Estevez, Abigail K. Switzer, Xiaonan Duan, Xuefei Yang, and Emmanuel P. Giannelis; Facile and Scalable Synthesis of Monodispersed Spherical Capsules with a Mesoporous Shell; *Chemistry of Materials Communication*; Apr. 6, 2010; p. 2693-p. 2695; vol. 22; Americal Chemical Society.
Juan Li, Jun Liu, Donghai Wang, Ruisong Guo, Xiaolin Li, and Wen Qi; Interfacially Controlled Synthesis of Hollow Mesoporous Silica Spheres with Radially Oriented Pore Structures; *Langmuir Article*; Jun. 24, 2010; p. 12267-p. 12272; vol. 26, No. 14; American Chemical Society.
Algaradah, "The Development of Nano-Sized Silicas as Analytical Tools", University of Southampton, Faculty of Natural and Environmental Sciences, School of Chemistry, Thesis for the Degree of Doctor of Philosophy, pp. 1, 54-55 and 119-122 (Nov. 2010).
Chang, "New Type of Mesoporous Silica Nanostructures: Synthesis, Structural and Morphological Control", National Tsing Hua University Institutional Repository, pp. 1, 32-33, 35, 38-43, 59-63, 74-79 and 80 with Abstract (2009).
Algaradah, "The Development of Nano-Sized Silicas as Analytical Tools", University of Southampton, Faculty of National and Environmental Sciences, School of Chemistry, Thesis for the Degree of Doctor of Philosophy, pp. 1, 54-55 and 119-122 (Nov. 2010).

* cited by examiner

*Primary Examiner* — Steven Bos
(74) *Attorney, Agent, or Firm* — Muncy, Geissler, Olds & Lowe, P.C.

(57) ABSTRACT

The present invention relates to a hollow sphere with a mesoporous structure, and a method for manufacturing the same. The hollow sphere with a mesoporous structure comprises: a shell with plural mesopores penetrating the shell, wherein the shell comprises: a mesoporous silicon oxide material, and mesopores of the mesoporous silicon oxide material are arranged in Ia3d cubic symmetry. In addition, according to the method of the present invention, the aforementioned hollow sphere with the mesoporous structure can be easily obtained by use of mixed surfactants of a cationic surfactant and a non-ionic surfactant.

13 Claims, 4 Drawing Sheets

HOLLOW SPHERE WITH MESOPOROUS STRUCTURE AND METHOD FOR MANUFACTURING THE SAME

CROSS REFERENCE TO RELATED APPLICATION

This application claims the benefits of the Taiwan Patent Application Serial Number 100110568, filed on Mar. 18, 2011, the subject matter of which is incorporated herein by reference.

BACKGROUND OF TI-E INVENTION

1. Field of the Invention

The present invention relates to a hollow sphere with a mesoporous structure and a method for manufacturing the same and, more particularly, to a hollow sphere and a method for manufacturing the same, wherein the mesopores of the material for forming a shell of the hollow sphere are arranged in Ia3d cubic symmetry.

2. Description of Related Art

Recently, studies on the mesoporous material are greatly developed, in order to develop various mesoporous materials with adjustable particle size, shapes, and pore arrangements. It has been known that when different surfactants or self-assembling materials are used, or when the reaction conditions are properly adjusted, the surface properties, the pore size, and the pore structures can be controlled. Owing to the tunable pore size and pore structure, the mesoporous material can carry various compounds, drugs, bio-agents, or nanoparticles, so the mesoporous material can be applied to various fields such as drug delivery, optical or magnetic resonance imaging, microcapsule, or catalytic reaction. For example, when the surface of the pore of the mesoporous material is modified with different functional groups, specific drugs can be absorbed on the surface through different intermolecular force. Furthermore, if the mesoporous material can be fabricated to become hollow, the loading amount can be largely increased. Although some studies have reported several synthetic methods for forming hollow and mesoporous spheres, the nano-sized pores are disordered. Therefore, it cannot be ensured that the hollow space is connected to the external space. Thereby, for releasing materials contained inside the hollow sphere, the releasing efficiency is not good enough.

When a hollow sphere with mesoporous structure is prepared by the method generally used in the art, core templates are first provided. Herein, the core template generally used can be a spherical hard template made of metals, metal oxides or polymers, or soft templates such as emulsions or carriers. Next, precursors and structure-directing agents are added into the reaction solution containing the core templates, and the precursors are polymerized on the outer surfaces of the core templates to form shells with mesoporous structures. In the case that the hard templates are used for preparing the hollow spheres with mesoporous structures, the particle size and the thickness of the shells of the hollow spheres can be precisely controlled. However, the hard templates have to be further removed, so the process is expensive and time-consuming. In cases that soft templates are used for the preparation of the hollow sphere with mesoporous structures, the process is complicated, and the particle size of the obtained hollow spheres is usually not uniform. Some reports have shown that the hollow spheres with mesoporous structures can be synthesized in one step, by using mixed anionic and cationic surfactants or fluoride-containing surfactants. However, the obtained hollow spheres shown in these reports do not have uniform particle size, and the thickness of the shells is difficult to control. In addition, the nanometer-sized pores are disordered. Therefore, it cannot be ensured that the hollow space is connected to the external space.

Furthermore, when the hollow spheres with mesoporous structures are applied to drug delivery, the particle size of the hollow spheres has to be 50-300 nm. However, it is difficult to prepare hollow spheres within the range of size by using the conventional methods in the art.

Therefore, it is desirable to provide a method for manufacturing hollow spheres, which can be used to prepare 50-300-nm, uniform and hollow spheres with communicating mesopores of the hollow space and the external space.

SUMMARY OF THE INVENTION

The object of the present invention is to provide a hollow sphere with a mesoporous structure, wherein there are plural mesopores penetrating through both surfaces of the shell of the hollow sphere. Hence, a purpose of releasing material inside the hollow sphere can be accomplished through the mesopores.

Another object of the present invention is to provide a method for manufacturing a hollow sphere with mesoporous structure, in order to prepare a hollow sphere with nano-size, and uniform particle size. In addition, the thickness of the shell, the diameter of the pores, and the property of the surface of the hollow sphere can be adjusted by use the method of the present invention.

To achieve the objects, the hollow sphere with a mesoporous structure of the present invention comprises: a shell with plural mesopores penetrating both surfaces of the shell, thereof, wherein the shell is made of a silicon dioxide material with orderly-arranged pores, and mesopores of the silicon dioxide material are arranged in Ia3d cubic symmetry.

In addition, the method for manufacturing the hollow sphere with the mesoporous structure of the present invention comprises the following steps: (A) providing an alkaline solution of mixed surfactants, wherein the mixed surfactants comprises a cationic surfactant and a non-ionic surfactant, the cationic surfactant is represented by the following formula (I), and the non-ionic surfactant is represented by the following formula (II):

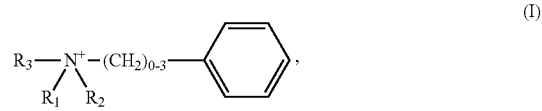

wherein, each $R_1$ and $R_2$ independently is a $C_1$-$C_3$ alkyl group, $R_3$ is a $C_{12}$-$C_{22}$ alkyl group, $R_4$ is a $C_{12}$-$C_{22}$ alkyl group, and n is an integer ranging from 2 to 20; and (B) adding a silane precursor into the alkaline solution of the mixed surfactants to make the silane precursor form into a hollow sphere with a mesoporous structure, wherein the hollow sphere comprises a shell with plural mesopores penetrating both surfaces of the shell, and the silane precursor is represented by the following formula (III):

wherein each $R_5$ independently is a $C_1$-$C_3$ alkyl group.

According to the hollow sphere with a mesoporous structure and the method for manufacturing the same of the present invention, the silane precursors can self-assemble into a hollow sphere through a simple process by using mixed surfactants of a cationic surfactant and a non-ionic surfactant. When the relative amount of each component in the reaction solution and other reaction condition is controlled, the outer diameter (i.e. particle size), and the thickness of the shell of the hollow sphere can be adjusted. In addition, when a hollow sphere with a mesoporous structure is prepared by use of the method of the present invention, the mesopores of the silicon dioxide material bi-continuously penetrate the shell of the hollow sphere and are arranged in Ia3d cubic symmetry. Therefore, it can be ensured that the mesopores of the hollow sphere of the present invention communicate the hollow space and the external space.

In addition, the method for manufacturing the hollow sphere with the mesoporous structure of the present invention may further comprise: adding at least one functional silane precursor into the alkaline solution of the mixed surfactants in the step (B). Herein, the functional silane precursor can be represented by the following formula (WI):

(VII)

wherein, $R_6$ is selected from the group consisting of $C_1$-$C_4$ alkyl group, $C_1$-$C_4$ alkoxy group, —$(CH_2)_{1-3}$—SH, —$(CH_2)_{1-3}$—CN, —$(CH_2)_{1-3}$—OCN, —$(CH_2)_{1-3}$—X, —$(CH_2)_{1-3}$—NH$_2$, and —$(CH_2)_{1-3}$—COOH, and X is Cl, Br, or I. Each $R_7$ independently is a $C_1$-$C_3$ alkyl group. Hence, the shell of the hollow sphere with the mesoporous structure of the present invention may further comprise surface-bound functional groups. Herein, the surface-bound functional groups may be selected from the group consisting of $C_1$-$C_4$ alkyl group, $C_1$-$C_4$ alkoxy group, —$(CH_2)_{1-3}$—SH, —$(CH_2)_{1-3}$—CN, —$(CH_2)_{1-3}$—OCN, —$(CH_2)_{1-3}$—X, —$(CH_2)_{1-3}$—NH$_2$, —$(CH_2)_{1-3}$—COOH, and X is Cl, Br, or I.

In one aspect of present invention, when the hollow sphere with the mesoporous structure is prepared by only using the silane precursor in the step (B), the amount of the silane precursor is 0.7-1 parts by mole, preferably. In another aspect of the method of the present invention, when the hollow sphere with the mesoporous structure is prepared by using the mixture of the silane precursor and the functional silane precursor, the amount of the silane precursor is 0.7-0.99 parts by mole, and the amount of the functional silane precursor is 0.01-0.3 parts by mole in the step (B).

According to the method for manufacturing the hollow sphere with the mesoporous structure of the present invention, preferably, each $R_7$ is the same group, and is a methyl group, an ethyl group, or a propyl group in the functional silane precursor represented by the following formula (VII). More preferably each $R_7$ is an ethyl group. In addition, preferably, $R_6$ is —$(CH_2)_{1-3}$—SH, or —$(CH_2)_{1-3}$—CN. More preferably, $R_6$ is —$(CH_2)_3$—SH, or —$(CH_2)_3$—CN. Hence, the surface-bound functional groups on the shell of the hollow sphere of the present invention preferably are —$(CH_2)_{1-3}$—SH, or —$(CH_2)_{1-3}$—CN. More preferably, the surface-bound functional groups are —$(CH_2)_3$—SH, or —$(CH_2)_3$—CN.

According to the method for manufacturing the hollow sphere with the mesoporous structure of the present invention, preferably, each $R_1$ and $R_2$ independently is a methyl group, an ethyl group, or a propyl group, and $R_3$ is a $C_{14}$-$C_{20}$ alkyl group in the cationic surfactant represented by the formula (I). More preferably, each $R_1$ and $R_2$ independently is a methyl group or an ethyl group, and $R_3$ is a $C_{14}$-$C_{20}$ alkyl group. Most preferably, the cationic surfactant is N-hexadecyl-N,N-dimethylbenzenaminium halide represented by the following formula (IV), N-benzyl-N,N-dimethylhexadecan-1-aminium halide represented by the following formula (V), or N,N-dimethyl-N-phenethylhexadecan-1-aminium halide represented by the following formula (VI):

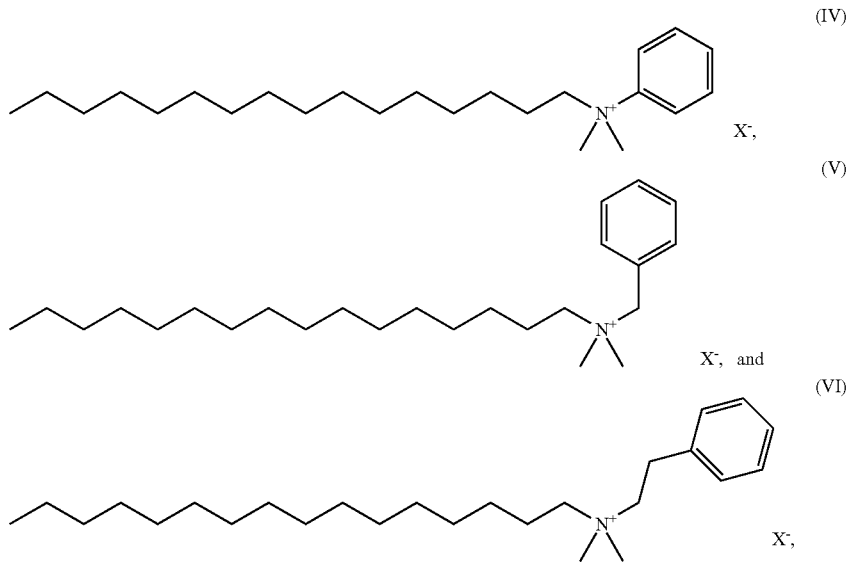

where $X^-$ is $Cl^-$ or $Br^-$.

In addition, according to the method for manufacturing the hollow sphere with the mesoporous structure of the present invention, preferably, $R_4$ is a $C_{14}$-$C_{20}$ alkyl group, and n is an integer ranging from 2 to 10 in the non-ionic surfactant represented by the formula (II). More preferably, $R_4$ is a $C_{14}$-$C_{18}$ alkyl group, and n is an integer ranging from 2 to 5. Most preferably, $R_4$ is a hexadecyl ($C_{1-6}$ alkyl) group, and n is an integer ranging from 2 to 3.

According to the method for manufacturing the hollow sphere with the mesoporous structure of the present invention, each $R_5$ independently can be a $C_1$-$C_3$ alkyl group in the silane precursor represented by the formula (III). Preferably, each $R_5$ is the same functional group, and is a methyl group, an ethyl group, or a propyl group. More preferably, each $R_5$ is an ethyl group. The specific examples of the precursors for silicon dioxide can be tetramethoxysilane (TMOS), tetraethoxysilane (TEOS), or tetrapropoxysilane (TPOS).

In the step (A) of the method for manufacturing the hollow sphere with the mesoporous structure of the present invention, the mixed surfactants in the alkaline solution may comprise: 0.065-0.095 parts by mole of the cationic surfactant, and 0.005-0.035 parts by mole of the non-ionic surfactant. In addition, the amount of water contained in the alkaline solution of the mixed surfactants may be 300-2000 parts by mole. When the amount of water, or the relative amount of each component in the reaction solution is adjusted, the outer diameter (i.e. particle size), and the thickness of the shell of the hollow sphere can be adjusted. Hence, the hollow sphere prepared through the method of the present invention preferably has a particle size of 50-300 nm. In addition, the thickness of the shell can be controlled in a range more than 5 nm, and the sphere even can be a solid sphere. Preferably, the thickness of the shell of the hollow sphere can be 5-50 nm.

In the step (A) of the method for manufacturing the hollow sphere with the mesoporous structure of the present invention, the alkaline solution of the mixed surfactants may further comprise: an inorganic base. Herein, the inorganic base can be LiOH, NaOH, KOH, RbOH, or $NH_4OH$. Preferably, the inorganic base is LiOH, NaOH, KOH, or $NH_4OH$. More preferably, the inorganic base is NaOH or $NH_4OH$. In addition, the amount of the inorganic base in the alkaline solution of the mixed surfactants preferably is 0.1-0.5 parts by mole. More preferably, the amount of the inorganic base in the alkaline solution of the mixed surfactants is 0.25-0.4 parts by mole.

According to the method for manufacturing the hollow sphere with the mesoporous structure of the present invention, the range of the reaction temperature in the step (B) is 25-50° C.

Other objects, advantages, and novel features of the invention will become more apparent from the following detailed description when taken in conjunction with the accompanying drawings.

DETAILED DESCRIPTION OF THE PREFERRED EMBODIMENT

The present invention has been described in an illustrative manner, and it is to be understood that the terminology used is intended to be in the nature of description rather than of limitation. Many modifications and variations of the present invention are possible in light of the above teachings. Therefore, it is to be understood that within the scope of the appended claims, the invention may be practiced otherwise than as specifically described.

Embodiment 1—Hollow Sphere Unmodified with Functional Groups 0.9 g of cationic surfactant, 576 ml of deionized water were added into a reaction flask, and stirred to dissolve at 35° C. In the present embodiment, the cationic surfactant was N-benzyl-N,N-dimethylhexadecan-1-aminium chloride.

Next, 0.3 g of non-ionic surfactant was added into the reaction solution, and stirred to dissolve at 35° C. In the present embodiment, the non-ionic surfactant was $C_{16}H_{33}(OC_2H_4)_2OH$.

0.0088 mole of inorganic base was added into the reaction solution containing the cationic surfactant and the non-ionic surfactant, and stirred to dissolve at 35° C. In the present embodiment, the inorganic base was NaOH. After the aforementioned steps, an alkaline solution of mixed surfactants was obtained.

Then, 5.98 ml of a silane precursor was added into the alkaline solution of the mixed surfactants. The reaction solution was stirred at 35° C. for 2-8 hrs, and aged at 70-90° C. for 1-3 days. In the present embodiment, the silane precursor is Tetraethoxysilane (TEOS).

Figure 1:
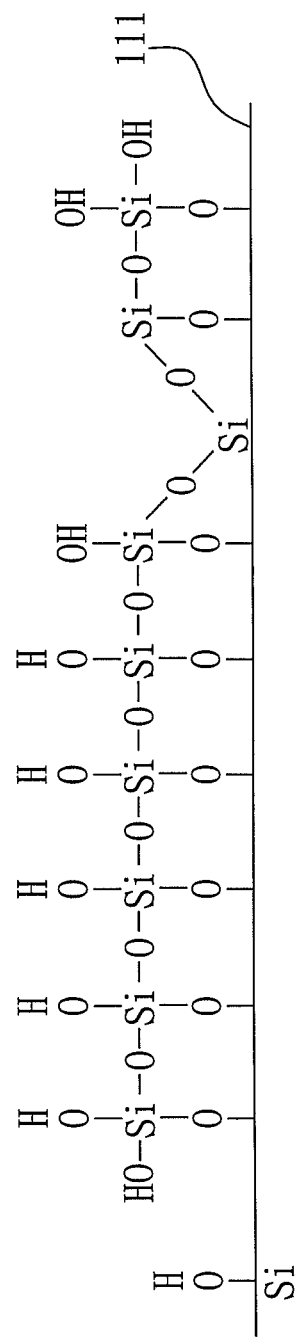
FIG. 1 is a perspective view showing a composition of a shell surface of a $SiO_2$ hollow sphere with a mesoporous structure according to Embodiment 1 of the present invention.

Finally, the reaction solution was filtered and dried, and the dried precipitant was the hollow spheres of the present embodiment. FIG. 1 is a perspective view showing a composition of a shell surface 111 of a $SiO_2$ hollow sphere with a mesoporous structure of the present embodiment.

Figure 2:
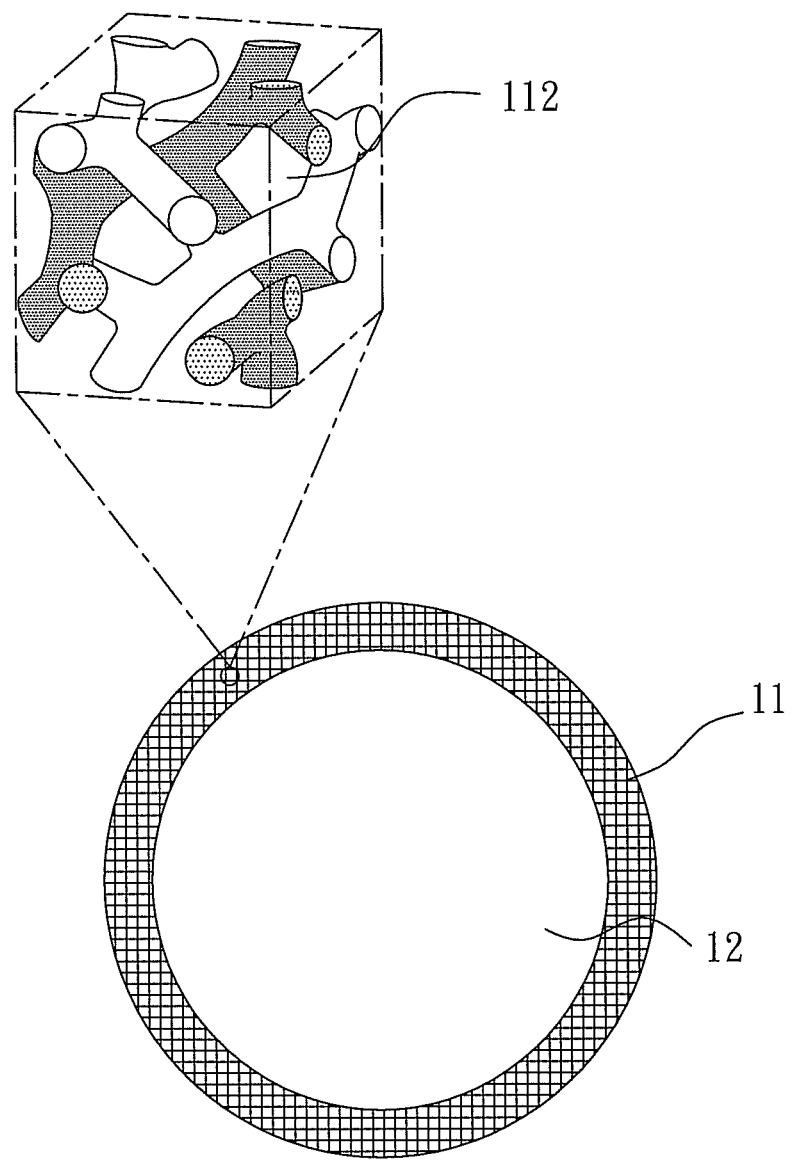
FIG. 2 is a cross-sectional views of a hollow sphere according to Embodiment 1 of the present invention.

In addition, when the hollow sphere of the present embodiment was analyzed with a transmission electron microscopy (TEM), the result showed that the hollow sphere indeed has a hollow part 12, and the particle size thereof is about 150 nm. Furthermore, the result of TEM also showed that the shell 11 of the hollow sphere of the present embodiment has orderly-arranged mesopores 112, and the perspective view of the shell is shown in FIG. 2.

Figure 3:
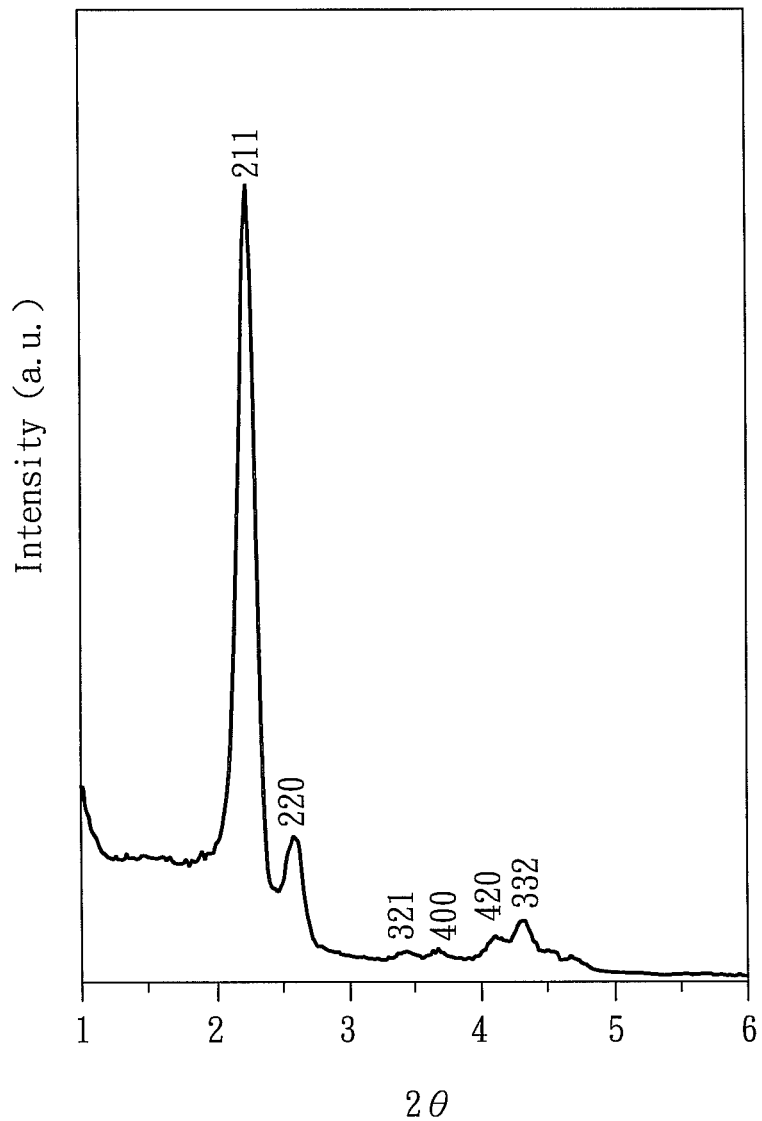
FIG. 3 is an X-ray diffraction diagram of a hollow sphere according to Embodiment 1 of the present invention.

When the powders of the hollow spheres were analyzed with X-ray diffraction (XRD), the XRD diagram shows that the mesopores of the $SiO_2$ material for forming the shell of the hollow sphere of the present embodiment are arranged in Ia3d cubic symmetry, as shown in FIG. 3.

Embodiment 2—Hollow Sphere Modified with Functional Groups

The method for preparing a hollow sphere of the present embodiment is the same as that described in Embodiment 1, except the cationic surfactant used in the present embodiment is N-hexadecyl-N,N-dimethylbenzenaminium chloride.

In addition, a functional silane precursor was added into the alkaline solution of the mixed surfactants, wherein the amount of TEOS was 5.38 ml, and the amount of functional silane precursor was 0.52 g. In the present embodiment, the functional silane precursor was $SH-(CH_2)_3-Si(OCH_3)_3$.

Figure 4:
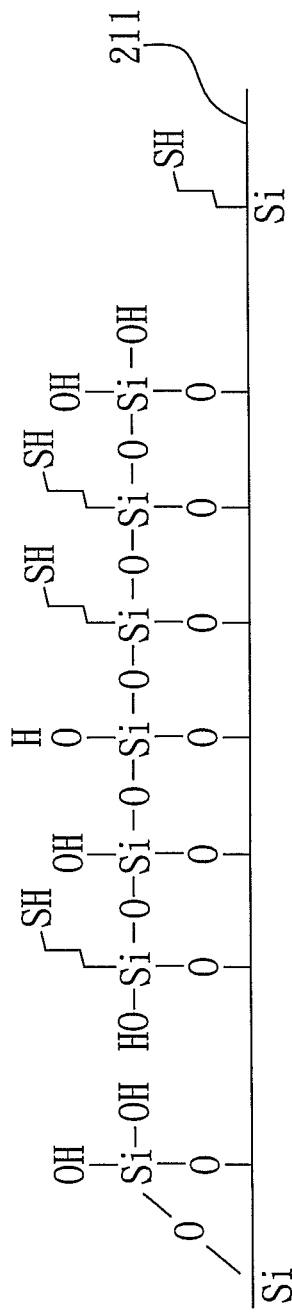
FIG. 4 is a perspective view showing a composition of a shell surface of a $SiO_2$ hollow sphere with a mesoporous structure according to Embodiment 2 of the present invention.

Hence, the shell 21 of the hollow sphere with the mesoporous structure of the present invention may further comprise the surface-bound functional group, ($-CH_2CH_2CH_2SH$). Herein, the surface 211, that the shell of the $SiO_2$ hollow sphere has functional groups binding thereto, is shown in FIG. 4

In addition, the results of TEM imaging and XRD diagram show that the particle size of the hollow sphere is about 100 nm, and the mesopores of the SiO, material for forming the shell of the hollow sphere are arranged in Ia3d cubic symmetry.

Embodiment 3—Hollow Sphere Modified with Functional Groups

The method for preparing a hollow sphere of the present embodiment is the same as that described in Embodiment 1, except the cationic surfactant used in the present embodiment is N-hexadecyl-N,N-dimethylbenzenaminium chloride.

In addition, another functional silane precursor was added into the alkaline solution of the mixed surfactants, wherein the amount of TEOS was 4.78 ml, and the amount of the functional silane precursor was 1.01 g.

In the present embodiment, the functional silane precursor was $CN-(CH_2)_3-Si(OCH_3)_3$.

Figure 5:
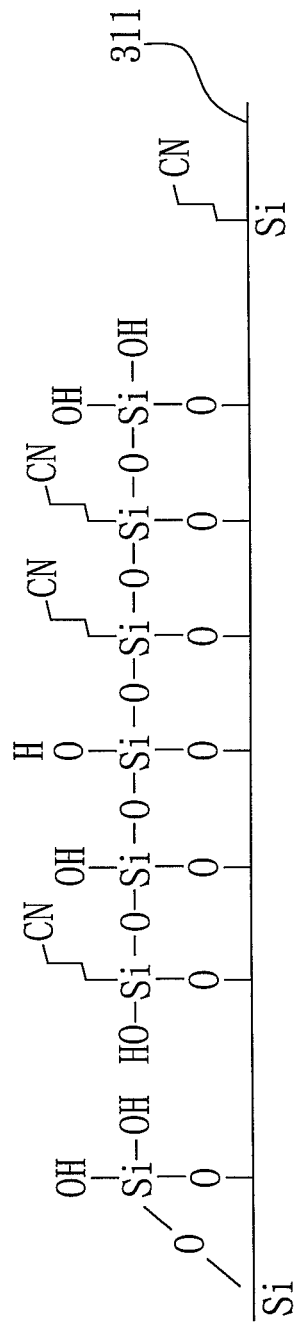
FIG. 5 is a perspective view showing a composition of a shell surface of a $SiO_2$ hollow sphere with a mesoporous structure according to Embodiment 3 of the present invention.

In the present embodiment, the shell 21 of the hollow sphere with the mesoporous structure of the present invention may further comprise the surface-bound functional group, ($-CH_2CH_2CH_2CN$). Herein, the surface 311, that the shell of the $SiO_2$ hollow sphere has functional groups binding thereto, is shown in FIG. 5.

Although the present invention has been explained in relation to its preferred embodiment, it is to be understood that many other possible modification and variations can be made without departing from the spirit and scope of the invention as hereinafter claimed.

What is claimed is:

1. A method for manufacturing a hollow sphere with a mesoporous structure, comprising the following steps:
    (A) providing an alkaline solution of mixed surfactants, wherein the mixed surfactants comprises a cationic surfactant and a non-ionic surfactant, the cationic surfactant is represented by the following formula (I), and the non-ionic surfactant is represented by the following formula (II):

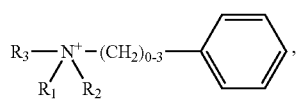  (I)

  (II), wherein, each $R_1$ and $R_2$ independently is a $C_1$-$C_3$ alkyl group, $R_3$ is a $C_{12}$-$C_{22}$ alkyl group, $R_4$ is a $C_{12}$-$C_{22}$ alkyl group, and n is an integer ranging from 2 to 20; and (B) adding a silane precursor and at least one functional silane precursor into the alkaline solution of the mixed surfactants and the functional silane precursor to form a hollow sphere with a mesoporous structure, wherein the hollow sphere comprises a shell with plural mesopores penetrating both surfaces of the shell, and the silane precursor and the functional silane precursor are respectively represented by the following formula (III) and formula (VII):

wherein $R_5$ is a $C_1$-$C_3$ alkyl group; and

wherein, $R_6$ is selected from the group consisting of a $C_1$-$C_4$ alkyl group, a $C_1$-$C_4$ alkoxy group, $-(CH_2)_{1-3}$-SH, $-(CH_2)_{1-3}$-CN, $-(CH_2)_{1-3}$-OCN, $-(CH_2)_{1-3}$-X, $-(CH_2)_{1-3}$-$NH_2$, and $-(CH_2)_{1-3}$-COOH, X is Cl, Br, or I, and each $R_7$ independently is a $C_1$-$C_3$ alkyl group.

2. The method as claimed in claim 1, wherein the alkaline solution of the mixed surfactants comprises: an inorganic base.

3. The method as claimed in claim 2, wherein the inorganic base is selected from the group consisting of LiOH, NaOH, KOH, RbOH, and $NH_4OH$.

4. The method as claimed in claim 1, wherein each $R_1$ and $R_2$ independently is a methyl group or an ethyl group, and $R_3$ is $C_{14}$-$C_{20}$ alkyl group.

5. The method as claimed in claim 4, wherein the cationic surfactant is selected from the group consisting of compounds represented by the following formulas (IV), (V), and (VI):

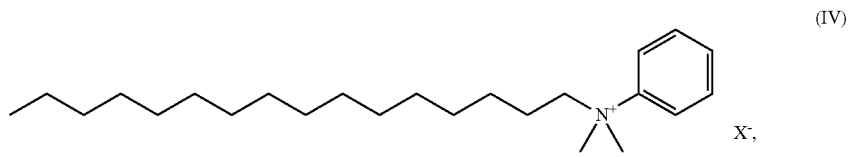  (IV)

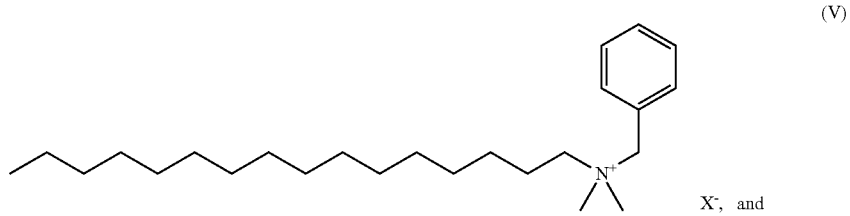  (V)

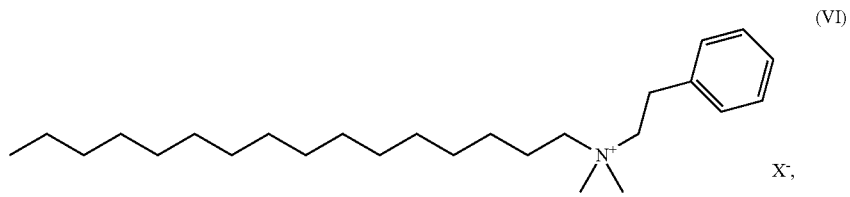  (VI)

wherein, $X^-$ is $Cl^-$, or $Br^-$.

6. The method as claimed in claim 1, wherein $R_4$ is a $C_{14}$-$C_{20}$ alkyl group, and n is an integer ranging from 2 to 10.

7. The method as claimed in claim 1, wherein $R_4$ is a hexadecyl group, and n is an integer ranging from 2 to 5.

8. The method as claimed in claim 1, wherein $R_5$ is a methyl group, an ethyl group, or a propyl group.

9. The method as claimed in claim 1, wherein each $R_7$ independently is a methyl group, an ethyl group, or a propyl group.

10. The method as claimed in claim 1, wherein $R_6$ is —$(CH_2)_{1-3}$—SH, or —$(CH_2)_{1-3}$—CN.

11. The method as claimed in claim 1, wherein the silane precursor reacts at a temperature range of 25-50 ° C. in the step (B).

12. The method as claimed in claim 1, wherein the alkaline solution of the mixed surfactants comprises: 0.065-0.095 parts by mole of the cationic surfactant, and 0.005-0.035 parts by mole of the non-ionic surfactant in the step (A).

13. The method as claimed in claim 1, wherein particle size of the hollow sphere is 50-300 nm.

* * * * *